United States Patent [19]

Caunt

[11] 3,940,345
[45] Feb. 24, 1976

[54] OLEFINE POLYMERIZATION CATALYST
[75] Inventor: Anthony David Caunt, Welwyn Garden City, England
[73] Assignee: Imperial Chemical Industries Limited, London, England
[22] Filed: June 4, 1973
[21] Appl. No.: 367,002

Related U.S. Application Data
[63] Continuation-in-part of Ser. No. 268,505, July 3, 1972, abandoned.

[30] Foreign Application Priority Data
July 13, 1971 United Kingdom............... 32856/71
June 9, 1972 United Kingdom............... 27010/72
Feb. 19, 1973 United Kingdom................ 7987/73

[52] U.S. Cl...... 252/429 B; 260/93.7; 260/346.1 R; 260/347.8; 260/551 P; 260/945
[51] Int. Cl.² B01J 27/14; B01J 27/16; B01J 31/12; B01J 31/14
[58] Field of Search ................................ 252/429 B

[56] References Cited
UNITED STATES PATENTS

| | | | |
|---|---|---|---|
| 3,186,977 | 6/1965 | Coover et al................. | 252/429 B X |
| 3,484,424 | 12/1969 | Moberly....................... | 252/429 B X |
| 3,511,891 | 5/1970 | Taylor et al.................. | 252/429 B X |
| 3,634,340 | 1/1972 | Gunther et al.............. | 252/429 B X |
| 3,658,779 | 4/1972 | Kahle et al................... | 252/429 B X |
| 3,766,160 | 10/1973 | Caunt........................... | 252/429 B X |

Primary Examiner—Patrick P. Garvin
Attorney, Agent, or Firm—Cushman, Darby & Cushman

[57] ABSTRACT

An olefine polymerisation catalyst includes a solid compound of a transition metal, e.g. titanium trichloride, an organo-compound of a non-transition metal, e.g. aluminium triethyl or diethyl aluminium chloride and a pentavalent phosphorus compound of the type $R_{3-n}P(Q)(E-Z-G)$, e.g.
$[(CH_3)_2N]_2P(O)N(CH_3)CH_2CH_2N(CH_3)_2$
and
$(CH_3)_2NP(O)[OCH_2CH_2N(CH_3)_2]_2$ The transition metal compound can be ball-milled in the presence of a further compound which can be the specified phosphorus compound or an electron donor compound, e.g., triphenylphosphine oxide. Using catalysts of this type, a combination of high activity and high stereospecificity can be obtained when polymerising an olefine monomer.

28 Claims, No Drawings

OLEFINE POLYMERIZATION CATALYST

This application is a continuation-in-part of Application Serial No. 268,505 filed 3 July 1972 and now abandoned.

The present invention relates to catalysts for the polymerisation of olefines and in particular to materials suitable for use as the third component in such catalysts and catalysts including such third components.

The low pressure polymerisation of olefines, particularly ethylene and propylene, to give high molecular weight polymers has been practised commercially for several years. The catalyst used for such polymerisations is commonly referred to as a "Ziegler" catalyst and this type of catalyst comprises a compound of a transition metal and an organo-metallic compound of aluminium or an element of Group I or II.

In order to obtain polymers having a high proportion of crystallinity the catalysts used normally comprise a solid compound of a transition metal, wherein the transition metal has a valency below its maximum, together with the organo-metallic compound. The transition metal compound is usually a halide and for the production of crystalline polymers the most widely used compound is titanium trichloride, which term is used to include pure titanium trichloride and also impure titanium trichloride associated or combined with other compounds, typically aluminium chloride, and produced by the reduction of titanium tetrachloride with, for example, aluminium metal or organo-aluminium compounds. The most extensively used organo-metallic compound is an organo-aluminium compound such as an aluminium trialkyl or an aluminium dialkyl halide.

Propylene can be polymerised with titanium trichloride and an organo-aluminium compound to give a high yield of polymer based on the catalyst used. However, the polymer produced still contains appreciable quantities of catalyst residues and for most applications it is necessary to remove most of these catalyst residues, this being done by washing with a suitable reagent to remove the catalyst. Typically, the polymer is first treated with an alcohol to terminate catalytic activity and then washed several times with water to remove the catalyst. Such catalyst removal operations increase the cost of producing the polymer.

Attempts have been made to eliminate the need to remove catalyst residues by polymerising the monomer to give a yield of polymer based on catalyst used which is considerably in excess of the yield normally obtained. When polymerising to such high yields the amount of catalyst remaining in the polymer is relatively small, for example, less than 50 parts per million by weight based on the polymer obtained. A disadvantage of polymerising to very high yields is that the polymer obtained has a tendency to contain a higher proportion of soluble polymer than is contained in polymer produced in the more normal yields.

Attempts have been made to reduce the proportion of soluble polymer produced by including a third component in the catalyst system. Whilst some of these third components do reduce the amount of soluble polymer produced, in many cases the polymerisation rate is adversely affected by the third component.

According to the present invention there is provided an olefine polymerisation catalyst comprising (1) a solid component of a transition metal wherein the said metal has a valency below its maximum, (2) an organo-metallic compound of aluminium or of a nontransition metal of Group II of the Periodic System, or a complex of an organo-metallic compound of a nontransition metal of Group I or II of the Periodic System and an organo-aluminium compound; and (3) a phosphorus compound of the formula

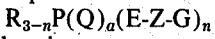

wherein
R is halogen, a hydrocarbyl group, a heterocyclic group or the group $-NR'_2$ or $-OR'$ where $R'$ is a hydrocarbyl group;
E is $-O-$, $-S-$, or $-NR'-$;
Z is a bivalent hydrocarbyl group such that E and G are separated by not more than 3 carbon atoms;
G is $-OR'$, $-SR'$, $NR'_2$, $PR'_2$ or a heterocyclic ring system whereof the heteroatom is O, S, N or P;
Q is an oxygen or sulphur atom;
$a$ is zero or one; and
$n$ is 1, 2 or 3.

The transition metal is a metal of Groups IVA to VIII of the Periodic Table preferably Groups IVA to VIA and can be for example, titanium, zirconium or vanadium. It is preferred that the transition metal compound is a transition metal halide or oxyhalide (for example $VOCl_2$) and it is particularly preferred to use titanium trichloride, especially a solid solution of titanium trichloride with aluminium chloride, for example the material obtained by reduction of $TiCl_4$ with aluminium metal as described in British Patent Specification 855 070, as component (1) of the catalyst. Component (2) can include Grignard reagents which are substantially ether free, $Mg(AlEt_4)_2$ or $Mg(C_6H_5)_2$. The aluminium compound can be lithium aluminium tetra alkyl and is preferably an aluminium hydrocarbyl halide, an aluminium hydrocarbyl sulphate, an aluminium hydrocarbyl oxyhydrocarbyl or particularly an aluminium trihydrocarbyl or dihydrocarbyl aluminium halide or hydride such as an aluminium trialkyl, a dialkyl aluminium halide or a dialkyl aluminium hydride, especially aluminium triethyl or diethyl aluminium chloride since catalysts including aluminium triethyl give a high polymerisation rate whilst catalysts including diethylaluminium chloride give a relatively low percentage yield of undesirable soluble ("atactic") polymer. As component (2), a mixture of compounds may be used, for example a mixture of an aluminium trialkyl and an aluminium dialkyl halide. Optionally the catalyst can include zinc hydrocarbyl compounds such as zinc diethyl or, in the presence of organo-aluminium compounds, zinc salts such as zinc chloride.

Thus, preferred catalysts in accordance with the present invention comprise (1) titanium trichloride, (2) an aluminium trihydrocarbyl or dihydrocarbyl aluminium halide or hydride, preferably aluminium triethyl or diethylaluminium chloride and, (3) a phosphorus compound of the formula

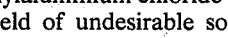

all as hereinbefore defined.

The proportions of the catalyst components can vary quite widely depending on the particular materials used and the absolute concentrations of the components. However, in general, for each molecular proportion of component (1), there may be present from 0.05 to 20 molecular proportions of component (2), and from 0.01 to 10 molecular proportions of component (3) with the amount of component (3) not being greater than the amount of component (2). For polymerisation to high yields we prefer to use 1 to 20 molecular proportions of component (2) and 0.1 to 4.0 molecular proportions of component (3).

In the phosphorus compound each hydrocarbyl group R' is preferably an alkyl group such as methyl or ethyl. The group R is conveniently an alkoxy group or a dialkyl amino group. If R is a heterocyclic group it can be pyridyl, pyrrolyl, pyrrolidyl or piperidyl and may be attached to the phosphorus atom through a carbon or nitrogen atom. It is preferred that Q is oxygen. It is also preferred that a is one.

The group (E-Z-G) can be, for example, an alkyl glycol, an alkanolamino, a diamino or an aminothiol group. G can be derived from a heterocyclic compound such as pyridine, quinoline, isoquinoline, furan, tetrahydrofuran, etc. We have obtained satisfactory polymerisation systems using, as the phosphorus compound, materials in which n has the value 1, 2 or 3.

Phosphorus compounds which can be used as third component of the catalyst include compounds of formulae I to XII P[OCH$_2$CH$_2$N(CH$_3$)$_2$]$_3$     I
P[N(CH$_3$)$_2$][OCH$_2$CH$_2$N(CH$_3$)$_2$]$_2$     II
P[N(CH$_3$)$_2$]$_2$[OCH$_2$CH$_2$N(CH$_3$)$_2$]     III

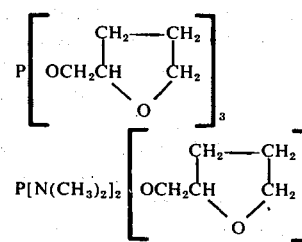
    IV

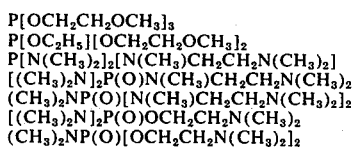
    V

P[OCH$_2$CH$_2$OCH$_3$]$_3$     VI
P[OC$_2$H$_5$][OCH$_2$CH$_2$OCH$_3$]$_2$     VII
P[N(CH$_3$)$_2$]$_2$[N(CH$_3$)CH$_2$CH$_2$N(CH$_3$)$_2$]     VIII
[(CH$_3$)$_2$N]$_2$P(O)N(CH$_3$)CH$_2$CH$_2$N(CH$_3$)$_2$     IX
(CH$_3$)$_2$NP(O)[N(CH$_3$)CH$_2$CH$_2$N(CH$_3$)$_2$]$_2$     X
[(CH$_3$)$_2$N]$_2$P(O)OCH$_2$CH$_2$N(CH$_3$)$_2$     XI
(CH$_3$)$_2$NP(O)[OCH$_2$CH$_2$N(CH$_3$)$_2$]$_2$     XII

As a further aspect the present invention also includes an olefine polymerisation process which comprises polymerising an olefine monomer using an olefine catalyst in accordance with the present invention.

More particularly an olefine monomer is polymerised using a catalyst comprising (1) a solid compound of a transition metal wherein the said metal has a valency below its maximum, preferably titanium trichloride, (2) an organometallic compound of aluminium or of a non-transition metal of Group II of the Periodic System, or a complex of a nontransition metal of Group I or II of the Periodic System and an organo-aluminium compound and is particularly an aluminium hydrocarbyl halide; an aluminium hydrocarbyl sulphate; an aluminium hydrocarbyl oxyhydrocarbyl or preferably an aluminium trihydrocarbyl or aluminium dihydrocarbyl halide or hydride compound especially aluminium triethyl or diethyl aluminium chloride, and (3) a phosphorus compound of the formula R$_{3-n}$P(Q)$_a$(E-Z-G)$_n$ where E, G, R, Q, Z, a and n are all as hereinbefore defined.

The phosphorus compound may be a compound of formulae I to XII as hereinbefore defined.

Any olefine monomer which is capable of being polymerised using a Ziegler catalyst may be polymerised using the process of the present invention. Thus olefine monomers which may be polymerised by the present process include butene-1 and 4-methyl pentene-1 and particularly propylene. The olefines may be copolymerised, either together or with ethylene, conveniently using a sequential polymerisation process as described in British Pat. Nos. 970 478 and 1 014 944.

We have found that the present process can be used for the polymerisation of propylene to give a high rate of polymerisation and a relatively low proportion of soluble polymer.

Thus, if propylene at a partial pressure of one atmosphere is polymerised using a catalyst comprising titanium trichloride, aluminium triethyl and a phosphorus compound of formulae I, II, V, IX or XII, after 2½ hours the yield of solid polymer obtained can be in excess of 20 gms, or even more than 30 gms, of polymer/millimole of TiCl$_3$ in the catalyst with the amount of soluble polymer produced being less than 15%, or even less than 10% by weight of the total polymer. Without the phosphorus compound and under otherwise the same conditions the yield of solid polymer is slightly greater than 30 gms/millimole of TiCl$_3$, but the amount of soluble polymer is about 29% by weight. Thus, the addition of the phosphorus compound has produced a substantial reduction in the proportion of soluble polymer produced to give a more acceptable proportion of soluble polymer. Generally the rate of polymerisation is also reduced by the addition of the phosphorus compound, but this reduction in rate is not such as to render the catalyst too inactive for satisfactory use. In some cases the presence of the phosphorus compound can actually increase the yield of the desired solid polymer, for example using a compound of formula II a yield of about 39 gms/millimole of TiCl$_3$ of solid polymer can be obtained under certain circumstances together with about 13.5% of soluble polymer.

The titanium trichloride used in the foregoing tests was the product of reducing titanium tetrachloride with aluminium. It has been found that the polymerisation rate and proportion of soluble polymer formed is dependent on the nature of titanium trichloride used and although the use of the reaction product of titanium tetrachloride and aluminium alkyl sesquihalide can give a high yield of solid polymer, a higher proportion of soluble polymer is also obtained with such catalysts.

The proportion of the phosphorus compound also affects the rate of polymerisation and proportion of soluble polymer produced. However, the nature of the phosphorus compound affects the proportion of phosphorus compound which is required to give the optimum effect.

If the phosphorus compound is a compound of trivalent phosphorus, that is a compound of formula
R$_{3-n}$P(E-Z-G)$_n$,
the effect of the phosphorus compound is believed to be dependent on the number of heteroatoms (that is O, S, N or P, other than the central P atom) present in the compound and in particular we have found that compounds containing O and/or N usually complex more strongly with the organo-metallic compounds such as the organo-aluminium compounds than with the transition metal of the transition metal compound such as titanium. Thus, using an organo-aluminium compound, the number of functional groups containing O and/or N should not exceed the amount of the aluminium compound and usually should be kept considerably less, for example 0.25 to 0.5 the amount of the aluminium compound. However, using the phosphorus compound in an amount such that the ratio of functional groups to transition metal, particularly Ti, is <0.25 does not produce the best catalyst. Thus, the minimum proportion of the phosphorus compound is dependent on the transition metal concentration and the upper limit is related to the concentration of the organo-metallic compound. More specifically, with a catalyst in which the trivalent phosphorus compound contains $f$ functional groups (that is O or N) per molecule, if the concentration of titanium trichloride is $C_T$ millimoles/liter and the concentration of aluminium triethyl is $C_A$ millimoles/liter, the concentration of the phosphorus compound is preferably in the range $$\frac{C_T}{4f} \text{ to } \frac{C_A}{2f} \text{ millimoles/litre}$$

Thus, if the basic catalyst system comprises 2 millimoles/liter of TiCl$_3$ and 4 millimoles/liter of aluminium triethyl, the concentration of a trivalent phosphorus compound containing 2 functional groups (that is, O or N atoms) per molecule is preferably in the range 0.25 to 1 millimole/liter and for a third component containing 4 functional groups, the concentration is preferably in the range 0.125 to 0.5 millimole/liter.

However, if the phosphorus compound is a compound of pentavalent phosphorus, that is a compound of formula
$$R_{3-n}P(Q)(E-Z-Q)_n,$$
the effect of the phosphorus compound is believed to be dependent primarily on the group P(Q) present in the compound. Thus using an organo-aluminium compound, the number of P(Q) groups should not exceed the amount of the aluminium compound and usually should be a little less than the amount of the aluminium compound used, for example 0.75 of the amount (in moles) of aluminium compound. However, using the pentavalent phosphorus compound in an amount such that the ratio of the P(Q) groups to Ti is <0.10 does not produce the best catalyst. Thus, the minimum proportion of the pentavalent phosphorus compound is also dependent on the titanium concentration and the upper limit is related to the concentration of the aluminium compound. More specifically, if the concentration of titanium trichloride is $C_T$ millimoles/liter and the concentration of aluminium triethyl is $C_A$ millimoles/liter, the concentration of the pentavalent compound is preferably in the range $$\frac{C_T}{10} \text{ to } \frac{3C_A}{4} \text{ millimoles/liter}$$

Thus, if the basic catalyst system comprises 2 millimoles/liter of TiCl$_3$ and 4 millimoles/liter of aluminium triethyl, the concentration of the pentavalent phosphorus compound is preferably in the range 0.2 to 3.0 millimoles/liter.

In carrying out polymerisations using catalysts in accordance with the invention the proportion of catalyst used is small in comparison to the amount of monomer being polymerised and thus is very susceptible to any impurities present in the system. Accordingly, in order to obtain the best possible results, all the materials used should be of high purity and all apparatus should be clean and free from any contamination which could affect the catalyst. Although the monomers and diluents used in the commercial production of polyolefines are sufficiently pure for use in the commercial processes, we find it is preferable to subject these materials, particularly the monomer, to a further purification treatment in order to obtain the best results. Many techniques are known for the purification of gases and liquids and any appropriate technique can be used. The technique used will depend in part on the purity of the starting materials and may involve the use of one or more stages. One purification technique which can be used is to contact the monomer, or diluent, with a material which is capable of absorbing impurities from the monomer or diluent, for example as described in British Pat. Specifications Nos. 1 111 493 and 1 226 659.

The catalysts of the present invention can be used to effect polymerisation in the presence of an inert diluent, for example, a paraffinic hydrocarbon, or in the absence of a diluent when polymerisation is effected either in the presence of excess liquid monomer or by contacting a gaseous monomer with the solid catalyst using any appropriate technique for effecting a gas/solid reaction such as a fluidised bed reactor. Furthermore, as is well known in the art, the polymerisation can be effected in the presence of a chain transfer agent to modify the molecular weight of the polymer, a suitable chain transfer agent being hydrogen.

The activity of the catalyst system may be increased by the use of the solid transition metal compound in a finely divided form. Suitable finely divided transition metal compounds can be obtained by grinding and very conveniently the grinding is effected by ball-milling the transition metal compound dry, for example as described in British Pat. Specifications Nos. 852 691 and 927 785.

We have found that useful improvements in the catalyst system are obtained if the transition metal component is ground, preferably ball-milled, together with an additional catalyst component. This additional component can be a phosphorus compound as hereinbefore defined. Alternatively, the additional component can be an electron donor compound of the type known to affect the catalyst activity and/or stereospecificity, such materials including amines, heterocyclic amines such as pyridine and quinoline, diamines, alkanolamines, amides, urea and derivatives thereof, organo-phosphorus compounds such as phosphines, phosphine oxides, phosphites and phosphates, organo-silicon compounds such as silanes and siloxanes, ethers, esters, ketones, alcohols and the sulphur containing analogues of such compounds such as thioethers, etc.

In addition to grinding the transition metal compound with an additional compound, a further quantity of the same, or a different, additional compound can be included in the catalyst system after the completion of the grinding step. This further addition of the additional component can produce a further improvement in the catalyst system and is a particularly preferred type of catalyst. It will be appreciated that in the foregoing catalyst systems, the phosphorus compounds as hereinbefore defined will be included either as the additional component ground with the transition metal compound or as the additional component added after the completion of the grinding. The same, or a different, phosphorus compound as hereinbefore defined can be used as both of such additional components.

If a further quantity of an additional compound is incorporated in a catalyst system which includes a transition metal compound which has been ground with an additional compound, it is desirable that this further quantity of additional compound is not allowed to contact the transition metal compound in the absence of at least some of the organo-metallic compound which is component (2) of the catalyst. Indeed, with the exception of the grinding process, it is generally preferred that the transition metal compound is not allowed to contact the phosphorus compound or the electron donor compound in the absence of the organo-metallic compound which is component 2) of the catalyst. The grinding of the transition metal compound and the phosphorus compound and/or electron donor compound is desirably effected using a molar excess of the transition metal compound, for example a molar ratio of transition metal compound to phosphorus compound or electron donor compound of 6:1; 9:1 or even greater.

A preferred catalyst system in accordance with the present invention comprises 1) a solid compound of a transition metal wherein the said metal has a valency below its maximum; (2) an aluminium trihydrocarbyl, an aluminium dihydrocarbyl hydride, an aluminium hydrocarbyl halide, an aluminium hydrocarbyl sulphate or an aluminium hydrocarbyl oxyhydrocarbyl; and (3) a phosphorus compound of the formula

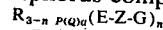
$R_{3-n}P(Q)_a(E-Z-G)_n$ where E, G, Q, R, Z, a and n are as hereinbefore defined, wherein the solid transition metal compound (1) has been modified by effecting grinding, preferably dry ball-milling, of the solid transition metal compound (1) with at least one additional compound which is either a phosphorus compound (3) or an electron donor compound of the type which affects the catalyst activity and/or stereospecificity.

A further preferred catalyst system in accordance with the present invention comprises (1) a solid compound of a transition metal wherein said metal has a valency below its maximum, (2) an aluminium trihydrocarbyl, an aluminium dihydrocarbyl hydride, an aluminium hydrocarbyl halide, an aluminium hydrocarbyl sulphate or an aluminium hydrocarbyl oxyhydrocarbyl; (3) a phosphorus compound of the formula

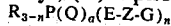
$R_{3-n}P(Q)_a(E-Z-G)_n$ where E, G, Q, R, Z, a and n are as hereinbefore defined. optionally (4) an electron donor compound of the type which affects the catalyst activity and/or stereospecificity, wherein the solid transition metal compound (1) has been modified by effecting grinding, preferably dry ball-milling, of the solid transition metal compound (1) with at least one compound which is a phosphorus compound (3), or an electron donor (4), and the catalyst contains a quantity of either the component (3) or component (4) or both components (3) and (4) in addition to the component (3) and/or (4) which is ground with the solid transition metal compound (1); said additional quantity of component (3) and/or (4) not being allowed to contact the modified transition metal compound in the absence of at least some of the organo-metallic compound (2).

Electron donors which may be used to modify the catalyst have been extensively described in the literature and the choice of a suitable electron donor can be made from those which have been described, although it will be realised that the effect of, and the optimum conditions for using, an electron donor will depend on the particular electron donor selected. Catalyst systems including electron donor compounds or complexes including electron donors are disclosed inter alia in British Pat. Specifications Nos. 803 198; 809 717; 880 998; 896 509; 920 118; 921 954; 933 236; 940 125; 966 025; 969 074; 971 248; 1 013 363; 1 049 723; 1 122 010; 1 150 845 and 1 208 815, Dutch Pat. application No. 70 15555 and German Pat. application No. 2 130 314. Alternatively the electron donor compound may be an essentially non-polar compound such as a cyclic polyene e.g., cycloheptatriene, cyclooctatriene or cyclooctatetrene.

It will be appreciated that the characteristics of the catalyst systems are dependent on a number of factors and that various phosphorus compounds of the type hereinbefore defined can produce catalysts having different activity and stereospecificity.

As a further aspect of the present invention there are provided new phosphorus compounds having the formula

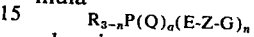
$R_{3-n}P(Q)_a(E-Z-G)_n$ wherein
R is halogen, a hydrocarbyl group, a heterocyclic group or the group $-NR'_2$ or $-OR'$ where R' is a hydrocarbyl group;
E is $-O-$, $-S-$ or $-NR'-$;
Z is a bivalent hydrocarbyl group such that E and G are separated by not more than 3 carbon atoms;
G is $-OR'$, $-SR'$, $-NR'_2$, $PR'_2$ or a heterocyclic ring system whereof the heteroatom is O, S, N or P;
Q is an oxygen or sulphur atom;
a is zero or one; and
n is 1, 2 or 3, with the exception that when a is 1, Q is oxygen and n is 1 or 2, not all the groups R are $-OR'$ groups.

Specifically there are provided as new materials compounds having the formula I to XII as hereinbefore defined.

A particular preferred feature of this aspect of the present invention is the provision of compounds of the general formula $P(E-Z-G)_3$.

Such compounds include the compounds represented by formulae I, IV and VI as hereinbefore defined.

As a further feature of the present invention, phosphorus compounds of the type defined can be prepared by the reaction of a compound H(E-Z-G), or a salt thereof, particularly the alkali metal salt, and a phosphorus compound

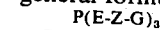
$R_3P(Q)_a$ where each R group is independently halogen, hydrocarbyl, heterocyclic, $-NR'_2$ or $-OR'$ and at least one of the groups R is $-NR'_2$, $-OR'$ or halogen. Preferably the phosphorus compound is of the type

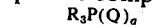
$R_{3-n}P(Q)_a(Ha)_n$ where Ha is halogen, preferably chlorine, and n is 1, 2 or 3. To prepare the preferred trivalent phosphorus compounds, that is those of the general formula
$P(E-Z-G)_3$, a phosphorus compound wherein all the groups R are the same is conveniently used.

The reaction between the compound $R_3P(Q)_a$ and the compound H(E—Z—G), or the salt thereof can be carried out in an inert diluent such as benzene, petroleum ether or diethyl ether or in the absence of a diluent, in an inert atmosphere such as argon or nitrogen, at a reaction temperature ranging from 0°C up to the boiling point of the diluent, or the boiling point of the mixture of reactants, which can be up to at least 240°C depending on the reactants. A convenient reaction temperature is in the range 0° to 100°C. The reaction occurs with the displacement of at least some of the groups R from the phosphorus compound as HR or the corresponding metal derivative. The extent of the reaction can be measured by titration of the displaced compound HR if HR is basic, e.g., an amine, or by fractional distillation and collection, e.g., where HR is ethanol. If the displaced compound HR is acidic the reaction is conveniently carried out in the presence of a compound which reacts with the HR to neutralise it, for example, if HR is a hydrogen halide the reaction can be carried out in the presence of a basic compound such as an amine, particularly a tertiary monoamine, and the amine hydrohalide thus formed is removed by filtration before separating the phosphorus compound. Alternatively the compound HR can be removed from the system as it is formed by the use of a continuous stream of an inert gas such as nitrogen. The reaction may proceed with the formation of a mixture of phosphorus compounds which may be separated by distillation under reduced pressure.

Phosphorus compounds of formula I, II, IV and VI have been characterised by elemental analysis, boiling point and density, and compounds of formula V, VII and VIII by boiling point and density. Compounds of formulae IX to XII have been characterised by boiling point, density and refractive index and the nuclear magnetic resonance data and the mass spectrum of these compounds was consistent with the formulae attributed to these materials. Nuclear magnetic resonance data on the compounds of formulae IV, V, VI and VII was consistent with the formulae attributed to these materials.

The following examples are illustrative of the various aspects of the present invention.

EXAMPLE 1

Preparation of P[OCH$_2$CH$_2$N(CH$_3$)$_2$]$_3$ and P[N(CH$_3$)$_2$][OCH$_2$CH$_2$N(CH$_3$)$_2$]$_2$ 27 millimoles of phosphorous hexamethyltriamide (P[N(CH$_3$)$_2$]$_3$) were added to 54 millimoles of N,N dimethyl ethanolamine in a flask in which an argon atmosphere was being maintained. A water-cooled reflux condenser was fitted to the flask which was heated on an oil bath at about 100°C whilst passing a stream of argon through the system. Dimethylamine was evolved and removed in the argon gas stream and the progress of the reaction was followed by titration of the dimethylamine with aqueous normal sulphuric acid. A total of 55.5 millimoles of base were evolved.

The mixture was then subjected to fractionation at a pressure of 0.2 mm of mercury when 6.2 millimoles of a compound identified as being of formula II were first recovered at a temperature between 68° and 70°C followed by 8.7 millimoles of a compound identified as being of formula I at a temperature between 89° and 92°C. The yield of the two compounds was 55% based on the original phosphorus compound. The residual contents of the reaction flask were a further quantity of the compound of formula I. Analysis of the contents of a cold trap included in the apparatus revealed 6 millimoles of a base which was believed to be unreacted dimethyl ethanolamine. Infra-red analysis of the two products revealed the presence of a minor proportion of impurities containing P=O and P—H bonding. The compounds were subjected to elemental analysis, the results of which were consistent with the formulae attributed to them.

EXAMPLE 2

Preparation of P[N(CH$_3$)$_2$]$_2$ [OCH$_2$CH$_2$N(CH$_3$)$_2$]

Into a reaction flask were placed, under an atmosphere of argon, 2 millimoles of phosphorous hexamethyltriamide in 20 ml of benzene and 2 millimoles of N,N dimethylethanolamine in 10 ml of benzene. The mixture was heated under reflux in a stream of argon and the progress of the reaction was followed by titration of the dimethylamine reaction byproduct with N/5 aqueous sulphuric acid. A further 20 ml of benzene was added when the reaction mixture boiled dry and the reaction was continued. After boiling dry again, a further 20 mls of benzene was added and the reaction was complete when a total of 2 millimoles of dimethylamine had been displaced. The reaction product which was believed to be of formula III, was a yellow oil which was soluble in benzene.

EXAMPLE 3

Preparation of P 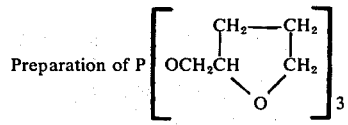

330 millimoles of tetrahydrofurfuryl alcohol were added, over a period of half an hour, to 300 milligramme atoms of sodium metal in 100 ml ether under nitrogen. A white solid was formed and the mixture was stirred. When the evolution of hydrogen was complete, 100 millimoles of phosphorus trichloride in 50 ml of ether were added over a period of half an hour. The ether boiled vigorously. The sodium chloride reaction product was allowed to settle overnight and the ether solution was decanted off. The sodium chloride was washed 4 times with ether to give a total of 750 ml of ether solution. The ether was distilled off at atmospheric pressure and the residue separated by fractionation in vacuo. The starting materials were first recovered followed by the reaction product. Elemental analysis and the nuclear magnetic resonance spectrum of the reaction product was consistent with a material of formula IV.

EXAMPLE 4

Preparation of P[N(CH$_3$)$_2$]$_2$ 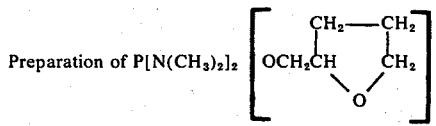

50 millimoles of phosphorous hexamethyltriamide (P[N(CH$_3$)$_2$]$_3$) were added to 50 millimoles of tetrahydrofurfuryl alcohol under an atmosphere of nitrogen. The mixture was heated under a water-cooled reflux condenser, and a stream of nitrogen. By-product dimethylamine was removed by the nitrogen stream and titrated with N sulphuric acid. Over a period of 10 hours, the temperature of the oil bath on which the mixture was being heated was raised to 240°C and a total of 26 milimoles of dimethylamine was displaced and measured by titration. The reaction mixture was separated by fractionation in vacuo to give 4.7 grammes of product the nuclear magnetic reasonance spectrum of which was consistent with a product of formula V.

EXAMPLE 5

Preparation of $P[OCH_2CH_2OCH_3]_3$ and $P(OC_2H_5)(OCH_2CH_2OCH_3)_2$ 300 millimoles of monomethylglycol were added to 100 millimoles of triethylphosphite under nitrogen. The mixture was heated to about 90°C with a fractionating column and condenser attached. 13.8 ml of ethanol was distilled over and the mixture remaining was then subjected to fractional distillation in vacuo. 7.8 grammes of a product having a nuclear magnetic resonance spectrum consistent with a product of formula VII was first obtained, followed by 1.4 grammes of a mixture of compounds and then 13.6 grammes of a product, the analysis and nuclear magnetic resonance spectrum of which was consistent with a product of formula VI.

EXAMPLE 6

Preparation of $P[N(CH_3)_2]_2[N(CH_3)CH_2CH_2N(CH_3)_2]$ 50 millimoles of phosphorous hexamethyltriamide $(P[N(CH_3)_2]_3)$ and 50 millimoles of N,N,N'-trimethylethylenediamine were mixed under nitrogen and heated under a water-cooled reflux condenser with a stream of nitrogen being passed over the reactants. The dimethylamine removed as a reaction by-product by the nitrogen was titrated with N sulphuric acid, a total of 18 millimoles of base being titrated. The reaction was terminated and the mixture subjected to fractional distillation in vacuo to recover first any unreacted materials and then 2.9 grammes of the reaction product. The product was believed to be of Formula VIII.

EXAMPLE 7

Preparation of $[(CH_3)_2N]_2P(O)N(CH_3)CH_2CH_2N(CH_3)_2$ 25 g (0.245 mole) N,N,N'-trimethylethylenediamine $(CH_3NHCH_2CH_2N(CH_3)_2)$ and 24.8 g(0.245 mole) triethylamine were charged into a 500 mls three-necked flask fitted with a stirrer, condenser, dropping funnel and nitrogen inlet. 150 mls of benzene was charged into the flask and the reaction mixture blanketed in nitrogen. A solution of 41.7 g (0.245 mole) bis(dimethylamino)chlorophosphine oxide $([CH_3)_2N]_2P(O)Cl.)$ in 50 mls benzene was then added to the contents of the flask. The reaction mixture was heated to reflux temperature (about 80°C) and maintained at this temperature for five hours after which heating was ceased and the mixture allowed to cool. Triethylamine hydrochloride was filtered off, washed with dry benzene and the washings added to the main bulk of the filtrate. The benzene was removed by evaporation in a rotary evaporator under reduced pressure (60 mm) and the liquid residue fractionally distilled under reduced pressure. The fraction distilling between 119°–120° at 1.0 mm was collected and subjected to analysis and characterisation. The yield of this fraction, which was identified as $[(CH_3)_2N]_2P(O)N(CH_3)CH_2CH_2N(CH_3)_2$, was 52% based on the original phosphorus compound.

EXAMPLE 8

Preparation of $(CH_3)_2NP(O)[N(CH_3)CH_2CH_2N(CH_3)_2]_2$. 25 g (0.244 mole) N,N,N'-trimethylethylenediamine and 25 g (0.247 mole) triethylamine were dissolved in 170 mls benzene and charged, under nitrogen, into a 500 ml three-necked flask fitted with a stirrer, condenser and dropping funnel. The reaction mixture was blanketed with dry nitrogen. 19.85 g (0.122 mole) dimethylaminodichlorophosphine oxide $((CH_3)_2NP(O)Cl_2)$ in 30 mls benzene was added, dropwise and with stirring, to the contents of the flask at a rate such that the reaction was maintained under control. The addition was completed in 30 minutes and the reaction mixture was then heated to reflux (about 80°C) for 30 minutes. Triethylamine hydrochloride was filtered off, washed with dry benzene and the washings combined with the main filtrate. The benzene was removed by evaporation in a rotary evaporator under reduced pressure (60 mm) and the residual liquid fractionally distilled under reduced pressure. The fraction distilling at 140°C (0.5 mm) was collected and subjected to analysis and characterisation which was consistent with the material being of the formula $(CH_3)_2NP(O)[N(CH_2CH_2N(CH_3)_2]_2$.

EXAMPLE 9

Preparation of $[(CH_3)_2N]_2P(O)OCH_2CH_2N(CH_3)_2$.

6.7 g (0.29 mole) sodium was cut into small pieces under petroleum ether (40–60) and added under a stream of dry nitrogen to 200 ml N,N-dimethylethanolamine contained in a 500 ml three-necked flask fitted with a stirrer, condenser and dropping funnel. When all the sodium had reacted the excess dimethylethanolamine was removed by vacuum distillation at 30°C and 0.1 to 0.5 mm. 100 mls of dry benzene were added to the solid residue which was thus dissolved. The reaction mixture was cooled in an ice bath and a solution of 50.0 g (0.29 mole) of bis-(dimethylamino)-chlorophosphine oxide $([(CH_3)_2N]_2P(O)Cl)$ in 50 ml benzene was added dropwise under nitrogen. On completion of the addition the reaction mixture was warmed to room temperature and stirred for 1 hour. Sodium chloride was formed as a precipitate which was filtered off. The filtrate was evaporated in a rotary evaporator under reduced pressure (60 mm) and the residual liquid fractionally distilled under reduced pressure (1 mm). The fraction distilling between 86°–88°C was collected and identified as $[(CH_3)_2N]_2P(O)OCH_2CH_2N(CH_3)_2$. The product was isolated in 64.4% yield.

EXAMPLE 10

Preparation of $(CH_3)_2NP(O)[OCH_2CH_2N(CH_3)_2]_2$.

9.3 g (0.404 mole) sodium was cut into small pieces under petroleum ether (40–60) and added under a stream of dry nitrogen to 200 ml N,N-dimethylethanolamine contained in a 500 ml three-necked flask fitted with a stirrer, condenser and dropping funnel. When all the sodium had reacted the excess dimethylethanolamine was removed by vacuum distillation at 30°C and 0.1 – 0.5 mm. 100 mls of dry benzene was added to the solid residue which dissolved and the solution obtained was cooled in an ice bath. A solution of 32.7 g (0.202 mole) dimethylaminodichlorophosphine oxide $((CH_3)_2NP(O)Cl_2)$ in 50 ml dry benzene was added dropwise under nitrogen to the cooled reaction mixture. On completion of the additive the reaction mixture was warmed to room temperature and the sodium chloride which precipitated was filtered off. The filtrate was evaporated in a rotary evaporator under reduced pressure (60 mm) and the residual liquid fractionally distilled under reduced pressure. The fraction distilling at 134°C (1.0 mm) was collected and identified as $(CH_3)_2NP(O)[OCH_2CH_2N(CH_3)_2]_2$. The product was isolated in 21% yield.

Various characteristics of the products obtained in Examples 1 to 10 were determined and these are set out in Table 1.

aluminium metal and thereafter ball-milling of the dry powder.)

A polymerisation flask equipped with efficient stirrer and a water jacket was dried carefully and 1 litre of an inert hydrocarbon diluent having a boiling range of about 170°–175°C was introduced. The diluent was

TABLE 1

| Compound Reference (a) | | Elemental Analysis (c) (wt %) | | | | | Boiling Point (°C/mmHG) | Density at 20°C (g/cm³) | NMR (c) | Mass Spectrum (c) | Refractive Index at 20°C |
|---|---|---|---|---|---|---|---|---|---|---|---|
| | | C | H | N | O | P | | | | | |
| I | calc.(b) | 48.7 | 10.2 | 14.2 | 16.2 | 10.4 | 89–92/0.2 | 0.984 | ND | ND | ND |
| | found | 48.4 | 10.6 | 15.0 | 15.7 | 10.3 | | | | | |
| II | calc.(b) | 47.7 | 10.4 | 16.7 | 12.7 | 12.3 | 68–70/0.2 | 0.976 | ND | ND | ND |
| | found | 47.3 | 10.4 | 16.3 | 14.1 | 11.9 | | | | | |
| IV | calc.(b) | 53.9 | 8.2 | — | 28.7 | 9.3 | 161–164/0.2 | 1.07 | YES | ND | ND |
| | found | 54.0 | 8.1 | — | 28.2 | 9.7 | | | | | |
| V | ND | | | | | | 72–75/0.15 | 1.02 | YES | ND | ND |
| VI | calc.(b) | 42.2 | 8.3 | — | 37.5 | 12.1 | 98–99/0.28 | 1.08 | YES | ND | ND |
| | found | 42.0 | 8.3 | — | 37.1 | 12.6 | | | | | |
| VII | ND | | | | | | 72–75/0.2 | 1.076 | YES | ND | ND |
| VIII | ND | | | | | | 87–90/0.23 | 0.919 | ND | ND | ND |
| IX | ND | | | | | | 120/1.0 mm | 1.013 | YES | YES | 1.468 |
| X | ND | | | | | | 140/0.5 mm | 1.014 | YES | YES | 1.472 |
| XI | ND | | | | | | 86/1.0 mm | 1.03 | YES | YES | 1.450 |
| XII | ND | | | | | | 134/1.0 mm | 0.95 | YES | YES | 1.448 |

NOTES TO TABLE 1 a. The compound references are as follows:

I product of Example 1, second material to be distilled off, formula corresponds to Formula I II product of Example 1, first material to be distilled off, formula corresponds to Formula II IV product of Example 3, formula corresponds to Formula IV V product of Example 4, formula corresponds to Formula V VI product of Example 5, second material to be distilled off, formula corresponds to Formula VI VII product of Example 5, first material to be distilled off, formula corresponds to Formula VII VIII product of Example 6, formula corresponds to Formula VIII IX product of Example 7, formula corresponds to Formula IX X product of Example 8, formula corresponds to Formula X XI product of Example 9, Formula corresponds to Formula XI XII product of Example 10, formula corresponds to Formula XII b. calculated on the basis of formula attributed to compound c. ND means not determined.

YES means NMR or Mass spectrum consistent with formula given.

EXAMPLES 11 to 35

The products of Examples 1 to 10 were then used as olefine polymerisation catalyst third components. The effect of the phosphorus compounds was tested in propylene polymerisations using triethyl aluminium and a commercially available form of titanium trichloride manufactured by Toho Titanium Company of Japan and identified as TAC 131. (This material is believed to be obtained by the reduction of $TiCl_4$ with aluminium metal and thereafter ball-milling of the dry powder.)

evacuated at 60°C purged with nitrogen and evacuated, which treatment effectively reduced the water and oxygen contents of the diluent to below 10 ppm by weight. The diluent was then saturated with propylene to one atmosphere pressure. The propylene used was obtained by the purification of an initial sample of propylene, containing methylacetylene and allene as impurities at levels well below 10 ppm by weight, by passing this propylene through a column of activated alumina. Triethyl-aluminium was introduced in the proportions indicated in Table 2 followed by the phosphorus compound to be tested. After half hour 2 millimoles of $TiCl_3$ were introduced. The pressure in the reaction vessel was maintained at one atmosphere by supply of propylene from a burette. After a further 2.5 hours the run was terminated with 10 ml of isopropanol and a sample of supernatant liquid extracted for determining the concentration of soluble polymer. The solid was filtered and washed three times with petrol ether and dried in a vacuum oven at 120°C for an hour. The yield of solid plus calculated soluble polymer equalled within experimental error the propylene lost from the burette.

The results obtained are set out in Table 2.

Comparative examples, indicated by letters, were carried out in a similar manner either omitting the phosphorus compound (A & B) or using a different compound.

NOTES TO TABLE 2 d. PHM is phosphorous hexamethyltriamide $(P[N(CH_3)_2]_3)$ e. Polymerisation would not proceed with 4 millimoles $AlEt_3$ f. Based on solid polymer only g. % based on total polymer (solid + soluble) formed.

\* In these experiments the titanium trichloride was TAC 141 supplied by Toho Titanium Company of Japan.

TABLE 2

| Example or Comparative Example | Phosphorus Compound Reference | Amount (mmol/l) | AlEt$_3$ (mmol/l) | Conversion to solid (g/mmol Ti) (f) | Soluble Yield (%) (g) |
|---|---|---|---|---|---|
| 11 | I | 0.25 | 4 | 30.5 | 13 |
| 12 | I | 0.8 | 8(e) | 26.5 | 11 |
| 13 | II | 0.5 | 4 | 39 | 13.5 |
| 14 | II | 1 | 8(e) | 30 | 11.5 |
| 15 | III | 1 | 4 | 28 | 17.5 |
| 16 | IV | 0.25 | 3.5 | 20 | 18 |
| 17 | IV | 0.75 | 7 | 15.5 | 14.5 |
| 18 | V | 0.5 | 4 | 33.5 | 14.5 |
| 19 | V | 1 | 4 | 14 | 13 |
| 20 | VI | 0.125 | 3.5 | 22 | 19.5 |
| 21 | VII | 0.2 | 3.5 | 15 | 20 |
| 22 | VIII | 0.5 | 4 | 14 | 16 |
| 23 | IX | 0.5 | 4 | 27.5 | 9.4 |
| 24 | IX | 1.0 | 4 | 24 | 7.3 |
| 25 | IX | 1.5 | 4 | 14.5 | 4.5 |
| 26 | IX | 1.5 | 5 | 22.7 | 6.7 |
| 27* | IX | 0.5 | 4 | 32.2 | 10.3 |
| 28* | IX | 1.0 | 4 | 22.2 | 8.0 |
| 29* | X | 0.25 | 4 | 32.2 | 17 |
| 30* | X | 0.5 | 4 | 30 | 14.2 |
| 31* | X | 1.0 | 4 | 15.0 | 9.2 |
| 32* | XI | 0.5 | 4 | 32.4 | 9.3 |
| 33* | XI | 1.0 | 4 | 28.1 | 8.5 |
| 34* | XII | 0.25 | 4 | 30.8 | 17.0 |
| 35* | XII | 0.5 | 4 | 31.4 | 11.7 |
| A | None | — | 3.5 | 22.5 | 30.5 |
| B | None | — | 4 | 33 | 29 |
| C* | None | — | 4 | 29.3 | 27.0 |
| D | PHM(d) | 0.1 | 4 | 5 | 30 |

EXAMPLES 36 to 41

Propylene polymerisations were also carried out with TiCl$_3$ obtained by reduction of TiCl$_4$ with ethylaluminium sesquichloride by the addition of 0.9 moles of the aluminium compound to 1.0 mole of TiCl$_4$, both compounds being dissolved in inert hydrocarbon diluent and maintained at 0°C during the presparation. The results obtained are set out in Table 3, in which the reference letters have the same significance as in Table 2.

Table 3

| Example or Comparative Example | Phosphorus Compound Reference | Amount (mmol/l) | AlEt$_3$ (mmol/l) | Conversion to solid (g/mmol Ti) (f) | Soluble Yield (%) (g) |
|---|---|---|---|---|---|
| 36 | I | 0.25 | 4 | 26 | 21.5 |
| 37 | II | 0.25 | 4 | 27 | 25 |
| 38 | IV | 0.25 | 4 | 13.5 | 24 |
| 39 | VI | 0.25 | 4 | 19 | 25 |
| 40 | VII | 0.25 | 4 | 16 | 20.5 |
| 41 | VIII | 0.25 | 4 | 17 | 21.5 |
| E | PHM(d) | 0.25 | 4 | 2.5 | 16.5 |
| F | None | — | 4 | 34 | 38.5 |

EXAMPLES 42 to 46

20 g (100 millimoles) of titanium trichloride manufactured by Toho Titanium Company of Japan and identified as TAC 141 were stirred in 100 cm$^3$ pentane under nitrogen and 3.7 millimoles of the phosphorus compound, reference I, were added over ½ hour. The mixture was transferred into a stainless steel ballmill with washing, and was then dried, in the mill, by removing the pentane under vacuo. The mill was 6 inches long and 3 inches in diameter and contained 200 stainless steel balls of half-inch diameter and 200 stainless steel balls of quarter-inch diameter. The mill was rotated at 120 rpm for 24 hours.

The catalyst was tested in propylene polymerisations using conditions similar to those described in Examples 11 to 35 except that 8 millimoles of aluminium triethyl was used. In one polymerisation, no further phosphorus compound was used apart from that introduced by the milling step. In other polymerisations a further quantity of a phosphorus compound or an electron donor compound was added in the manner set out in Examples 11 to 35. The nature and amount of the further addition of phosphorus compound or electron donor compound are set out in Table 4 together with the results obtained.

TABLE 4

| Example | Further Compounds Added | | Conversion to Solid (g/mmol) (f) | Soluble Yield (%) (g) |
|---|---|---|---|---|
| | Compound (h) | Amount (mmol/l) | | |
| 42 | None | Nil | 47 | 12.3 |
| 43 | I | 0.33 | 36.5 | 8.8 |
| 44 | II | 0.33 | 46.5 | 7.9 |
| 45 | Isoquinoline | 4 | 39.5 | 10.4 |
| 46 | TMED | 1 | 26.2 | 6.9 | h)
I is the phosphorus compound of Formula I
II is the phosphorus compound of Formula II
TMED is tetramethylethylenediamine

EXAMPLES 47 TO 49

The transition metal compound was ball-milled with an electron donor compound.

The transition metal compound was TAC 121 titanium trichloride supplied by the Toho Titanium Company of Japan and the electron donor was triphenyl phosphine oxide. The compounds were added directly to the mill in the solid form, the titanium trichloride being added first. The mill used was 9 inches long and 5.1 inches diameter and contained 685 steel balls of ½ inch diameter. The molar ratio of titanium trichloride to triphenyl phosphine oxide was 6:1 and milling was effected at 64 rpm foor 65 hours. A nitrogen atmosphere was maintained in the mill at all times during loading, milling and unloading.

Polymerisations were carried out as described in respect of Example 43 with the addition of the indicated quantity of the phosphorus compound, reference I or IX. A comparative example (Example G) was carried out in the absence of a further phosphorus compound. The results obtained are set out in Table 5.

TABLE 5

| Example or Comparative Example | Phosphorus Compound Ref | Amount (mmol/l) | Conversion to Solid g/mmol (f) | Soluble Yield (%) (g) |
|---|---|---|---|---|
| G | Nil | Nil | 75 | 11.4 |
| 47 | I | 0.33 | 59.5 | 5.2 |
| 48 | I | 0.66 | 62.5 | 4.2 |
| 49 | IX | 1.5 | 50 | 4.1 |

EXAMPLE 50 and 51

The effect of ball-milling the transition metal compound with a pentavalent phosphorus compound of the type defined was also studied.

The milling was carried out in the same mill as was used in Examples 42 to 46. The transition metal compound was TAC 141 titanium trichloride supplied by Toho Titanium Company of Japan and the phosphorus compound was the product of Example 7. The two materials were introduced into the mill as a slurry in pentane, which was evaporated off before commencing the milling. The molar ratio TAC 141 to phosphorus compound was 9:1 and milling was effected at 120 rpm for 24 hours. A nitrogen atmosphere was maintained in the mill throughout.

Polymerisation was carried out as described in Examples 42 to 46, in one experiment with no additional phosphorus compound and in a further polymerisation with a further quantity (1.5 millimoles) of the phosphorus compound, this further quantity being added shortly after the aluminium triethyl and half and hour before adding the milled titanium trichloride.

The results obtained are set out in Table 6.

TABLE 6

| Example No. | Fourth Component (mmol) (i) | Conversion to solid polymer (g/mmol Ti) (f) | Soluble Yield (%) (g) |
|---|---|---|---|
| 50 | Nil | 56 | 6.8 |
| 51 | 1.5 | 51 | 4.2 |

(f) (g) see Table 2.
(i) The fourth component was the product of Example 7.

EXAMPLE 52

30 gms of a sample of pure $TiCl_3$ produced by hydrogen-reduction of $TiCl_4$ were activated by milling under nitrogen in a stainless-steel mill 3 inches dimater, 6 inches long containing 200 half-inch and 200 quarter inch stainless steel balls. The mill was rotated at 120 rpm for 24 hours.

Propylene was polymerised with this catalyst under conditions similar to those described in Examples 50 and 51. Polymerisation in presence of 1.5 mmol/l of the product of Example 7 yielded 21 grams of solid polymer and the diluent contained soluble polymer corresponding to 8.7% of the total.

A comparison run in which the product of Example 7 was omitted yielded 23 grams of solid polymer and 28.3% of soluble polymer.

If the unmilled titanium trichloride is used, in the absence of a phosphorus compound, in a polymerisation process as described in Examples 11 to 35 the yield of solid polymer is about 2.5 gms/millimole Ti and about 25 to 28% of soluble polymer.

EXAMPLE 53

A catalyst system was used wherein a cyclic polyene was incorporated as a fourth catalyst component.

The procedure used was generally as described in respect of Examples 11 to 35 except that the titanium trichloride was Stauffer AA (manufactured by Stauffer Chemical Company and believed to be the product of reacting titanium tetrachloride with aluminium metal and ball-milling the dry powder) and the cyclic polyene (which was cycloheptatriene - CHT) was included in the catalyst system. The CHT was added to the aluminium triethyl before the phosphorus compound (compound of formula IX) was added. Comparative examples were carried out in which the phosphorus compound was omitted and also in which both the phosphorus compound and the CHT were omitted. The results are set out in Table 7.

TABLE 7

| Example or Comparative Example | Amount Phosphorus Compound (mmol/l) | Amount CHT (mmol/l) | Conversion to Solid Polymer (g/mmol Ti) (f) | Soluble Yield (%) (g) |
|---|---|---|---|---|
| 53 | 1 | 2 | 16 | 5.1 |
| H | Nil | 2 | 14 | 9.3 |
| J | Nil | Nil | 32.5 | 29.3 |

(f) (g) see Table 2

EXAMPLES 54 and 55

The effect of phosphorus compounds was tested in propylene polymerisation using diethylaluminium chloride and Stauffer AA grade titanium trichloride.

The polymerisation conditions were as described for Examples 11 to 35 but using 10 mmol $Et_2AlCl$ and 5 mmol $TiCl_3$ per liter of inert diluent, and a polymerisation time of 3 hours.

The results are set out in Table 8. Comparative example K was carried out in a similar manner but omitting the phosphorus compound.

EXAMPLE 56

A propylene polymerisation was carried out with a catalyst obtained by reduction of $TiCl_4$ with ethyl aluminium sesquichloride by the slow addition of 0.9 moles of aluminium compound to 1.0 mole of TiCl₄, both compounds being dissolved in an inert hydrocarbon diluent, the mixture being stirred initially at 0°C. After 6 hours the temperature of the catalyst preparation was raised to 110°C, after 4 hours the slurry was cooled and washed with the inert hydrocarbon. The TiCl₃ product obtained was used to polymerise propylene as in Examples 54 and 55 using 2 millimoles of compound XI. A polymer yield of 7.3 gm/mmol of TiCl₃ with 0.36% of soluble polymer was obtained. In the absence of the phosphorus compound the yield was 8.3 gm/mmol and the amount of solubles 1%.

TABLE 8

| Example or Comparative Example | Phosphorus Compound Reference | Amount (mmol/l) | Conversion to Solid Polymer (g/mmol Ti) (f) | Soluble Yield (%) (g) |
|---|---|---|---|---|
| 54 | IX | 1 | 8.5 | 3.9 |
| 55 | XI | 2 | 8.9 | 1.7 |
| K | None | — | 6.0 | 3.1 |

I claim:
1. An olefine polymerisation catalyst consisting essentially of
   1. one molecular proportion of a solid halide of titanium, vanadium or zirconium wherein the metal has a valency below its maximum,
   2. from 0.05 up to 20 molecular proportions of at least one compound selected from the group consisting of Grignard reagents which are substantially ether free, Mg[Al(C₂H₅)₄]₂, Mg(C₆H₅)₂, lithium aluminium tetraalkyls, aluminium hydrocarbyl halides, aluminium hydrocarbyl sulphates, aluminium hydrocarbyl oxyhydrocarbyls, aluminium trihydrocarbyls and dihydrocarbyl aluminium hydrides, and
   3. from 0.01 up to 10 molecular proportions of at least one phosphorus compound of the formula
   $R_{3-n}P(Q)(E-Z-G)_n$
wherein
   R is halogen, hydrocarbyl group, pyridyl, pyrrolyl, pyrrolidyl, piperidyl group, the group —NR′₂ or —OR′,
   E is —O—, —S—, or —NR′—;
   Z is a bivalent hydrocarbyl group such that E and G are separated by not more than 3 carbon atoms;
   G is —OR′, —SR′, —NR′₂, —PR′₂, a pyridyl radical, a quinolyl radical, an isoquinolyl radical, a furyl radical or a tetrahydrofuryl radical;
   R′ is a hydrocarbyl group;
   Q is an oxygen or sulphur atom; and
   n is 1, 2, or 3, and wherein the amount of component (3) is not greater than the amount of component (2).

2. The catalyst of claim 1 wherein component (1) is titanium trichloride.
3. The catalyst of claim 1 wherein component (2) is an aluminium trihydrocarbyl, an aluminium dihydrocarbyl halide or an aluminium dihydrocarbyl hydride.
4. The catalyst of claim 1 wherein component (1) is titanium trichloride, and component (2) is aluminium triethyl or aluminium diethyl chloride.
5. The catalyst of claim 1 wherein in component (3) each group R′ is a methyl or ethyl group.
6. The catalyst of claim 1 wherein in component (3) the group R is an alkoxy group or a dialkyl amino group.

7. The catalyst of claim 1 wherein component (1) has been ground in the dry state.
8. The catalyst of claim 7 wherein the solid halide which is component (1) has been ground with at least part of component (3) or with triphenyl phosphine oxide in a molar ratio of solid halide to component (3) or triphenyl phosphine oxide of at least 6:1.
9. The catalyst of claim 8 wherein, in addition to the materials ground with component (1), the catalyst further contains a quantity of at least one compound selected from the group consisting of component (3), pyridine, quinoline, isoquinoline, tetramethylethylenediamine and triphenyl phosphine oxide said quantity being a minor amount sufficient to improve the catalyst activity, stereospecificity or both and the quantity of component (3) being the remainder of component (3).
10. The catalyst of claim 9 wherein component (1) is not allowed to contact component (3), pyridine, quinoline, isoquinoline, tetramethylethylenediamine or triphenylphosphine oxide in the absence of component (2) of the catalyst other than when the solid halide is ground with component (3), pyridine, quinoline, isoquinoline, tetramethylethylenediamine or triphenylphosphine oxide.
11. The catalyst of claim 8 wherein the solid halide is titanium trichloride and component (2) is an aluminium trihydrocarbyl, an aluminium dihydrocarbyl halide or an aluminium dihydrocarbyl hydride.
12. The catalyst of claim 11 further containing a component (4) selected from the group consisting of pyridine, quinoline, isoquinoline, tetramethylethylenediamine and triphenylphosphine oxide, and wherein (a) component (1) is titanium trichloride which has been dry ball-milled with at least one compound selected from the group consisting of component (3), component (4), and mixtures thereof in a molar ratio of component (1) to component (4) of at least 6:1; and
   b. in addition to said compound dry ball-milled with titanium trichloride, the catalyst contains an additional quantity of component (3), component (4), or mixtures thereof which quantity has not been allowed to contact component (1) in the absence of at least some of component (2), the quantity of component (4) being a minor amount sufficient to improve the catalyst activity, stereospecificity, or both, and the quantity of component (3) being the remainder of component (3).
13. The catalyst of claim 4 wherein the component (3) is
   [(CH₃)₂N]₂P(O)N(CH₃)CH₂CH₂N(CH₃)₂;
   (CH₃)₂NP(O)[N(CH₃)CH₂CH₂N(CH₃)₂]₂ ;
   [(CH₃)₂N]₂P(O)OCH₂CH₂N(CH₃)₂ ; or
   (CH₃)₂NP(O)[OCH₂CH₂N(CH₃)₂]₂.
14. The catalyst of claim 11 wherein component (1) is titanium trichloride which has been ball-milled with
   [(CH₃)₂N]₂P(O)N(CH₃)CH₂CH₂N(CH₃)₂
wherein the molar ratio of titanium trichloride to
   [(CH₃)₂N]₂P(O)N(CH₃)CH₂CH₂N(CH₃)₂
is at least 6:1.
15. In an olefine polymerisation catalyst consisting essentially of
   1. a solid halide of titanium, vanadium or zirconium wherein the metal has a valency below its maximum, and
   2. at least one compound selected from the group consisting of Grignard reagents which are substantially ether free, Mg[Al(C$_2$H$_5$)$_4$]$_2$, Mg(C$_6$H$_5$)$_2$, lithium aluminium tetraalkyls, aluminium hydrocarbyl halides, aluminium hydrocarbyl sulphates, aluminium hydrocarbyl oxyhydrocarbyls, aluminium trihydrocarbyls and dihydrocarbyl aluminium hydrides, the improvement of adding 3. from 0.01 up to 10 molecular proportions for each molecular proportion of the solid halide of at least one phosphorus compound of the formula $R_{3-n}P(Q)(E-Z-G)_n$ wherein R is halogen, hydrocarbyl group, pyridyl, pyrrolyl, pyrrolidyl, piperidyl group, the group —NR'$_2$ or —OR';

E is —O—, —S—, or —NR'—;

Z is a bivalent hydrocarbyl group such that E and G are separated by not more than 3 carbon atoms;

G is —OR', —SR', —NR'$_2$, —PR'$_2$, a pyridyl radical, a quinolyl radical, an isoquinolyl radical, a furyl radical or a tetrahydrofuryl radical, R' is a hydrocarbyl group;

Q is an oxygen or sulphur atom; and $n$ is 1, 2, or 3, and wherein the amount of component (3) is not greater than the amount of component (2).

16. The catalyst of claim 15 wherein component (1) is titanium trichloride.

17. The catalyst of claim 15 wherein component (2) is an aluminium trihydrocarbyl, an aluminium dihydrocarbyl halide or an aluminium dihydrocarbyl hydride.

18. The catalyst of claim 15 wherein component (1) is titanium trichloride, and component (2) is aluminium triethyl or aluminium diethyl chloride.

19. The catalyst of claim 15 wherein in component (3) each group R' is a methyl or ethyl group.

20. The catalyst of claim 15 wherein in component (3) the group R is an alkoxy group or a dialkyl amino group.

21. The catalyst of claim 15 wherein component (3) is

[(CH$_3$)$_2$N]$_2$P(O)N(CH$_3$)CH$_2$CH$_2$N(CH$_3$)$_2$;
(CH$_3$)$_2$NP(O)[N(CH$_3$)CH$_2$CH$_2$N(CH$_3$)$_2$]$_2$;
[(CH$_3$)$_2$N]$_2$P(O)OCH$_2$CH$_2$N(CH$_3$)$_2$; or
(CH$_3$)$_2$NP(O)[OCH$_2$CH$_2$N(CH$_3$)$_2$]$_2$.

22. The catalyst of claim 15 wherein component (1) has been ground in the dry state.

23. The catalyst of claim 22 wherein the solid halide which is component (1) has been ground with at least part of component (3) or with triphenyl phosphine oxide in a molar ratio of solid halide to component (3) or triphenyl phosphine oxide of at least 6:1.

24. The catalyst of claim 23 wherein, in addition to the materials ground with component (1), the catalyst further contains a quantity of at least one compound selected from the group consisting of component (3), pyridine, quinoline, isoquinoline, tetramethylethylenediamine and triphenyl phosphine oxide said quantity being a minor amount sufficient to improve the catalyst activity, stereospecificity or both, and the quantity of component (3) being the remainder of component (3).

25. The catalyst of claim 24 wherein component (1) is not allowed to contact component (3), pyridine, quinoline, isoquinoline, tetramethylethylenediamine or triphenylphosphine oxide in the absence of component (2) of the catalyst other than when the solid halide is ground with component (3), pyridine, quinoline, isoquinoline, tetramethylethylenediamine or triphenylphosphine oxide.

26. The catalyst of claim 23 wherein the solid halide is titanium trichloride and component (2) is an aluminium trihydrocarbyl, an aluminium dihydrocarbyl halide or an aluminium dihydrocarbyl hydride.

27. The catalyst of claim 26 further containing a component (4) selected from the group consisting of pyridine, quinoline, isoquinoline, tetramethylethylenediamine and triphenylphosphine oxide, and wherein (a) component (1) is titanium trichloride which has been dry ball-milled with at least one compound selected from the group consisting of component (3), component (4), and mixtures thereof in a molar ratio of component (1) to component (4) of at least 6:1; and b. in addition to said compound dry ball-milled with titanium trichloride, the catalyst contains an additional quantity of component (3), component (4), or mixtures thereof which quantity has not been allowed to contact component (1) in the absence of at least some of component (2), the quantity of component (4) being a minor amount sufficient to improve the catalyst activity, stereospecificity, or both, and the quantity of component (3) being the remainder of component (3).

28. The catalyst of claim 26 wherein component (1) is titanium trichloride which has been ball-milled with

[(CH$_3$)$_2$N]$_2$P(O)N(CH$_3$)CH$_2$CH$_2$N(CH$_3$)$_2$ wherein the molar ratio of titanium trichloride to

[(CH$_3$)$_2$N]$_2$P(O)N(CH$_3$)CH$_2$CH$_2$N(CH$_3$)$_2$ is at least 6:1.

* * * * *